United States Patent
She et al.

(10) Patent No.: US 10,309,978 B2
(45) Date of Patent: Jun. 4, 2019

(54) SAMPLE RACK MOVING MECHANISM, SAMPLE RACK CONVEYING DEVICE AND SAMPLE ANALYZING EQUIPMENT

(71) Applicant: SHENZHEN MINDRAY BIO-MEDICAL ELECTRONICS CO., LTD., Shenzhen (CN)

(72) Inventors: Fating She, Shenzhen (CN); Leping Zhang, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 166 days.

(21) Appl. No.: 15/295,892

(22) Filed: Oct. 17, 2016

(65) Prior Publication Data
US 2017/0030938 A1 Feb. 2, 2017

Related U.S. Application Data
(63) Continuation of application No. PCT/CN2014/075617, filed on Apr. 17, 2014.

(51) Int. Cl.
G01N 35/02 (2006.01)
G01N 35/04 (2006.01)

(52) U.S. Cl.
CPC .......... *G01N 35/026* (2013.01); *G01N 35/04* (2013.01); *G01N 2035/0415* (2013.01); *G01N 2035/0484* (2013.01); *G01N 2035/0486* (2013.01)

(58) Field of Classification Search
CPC ............... G01N 35/026; G01N 35/04; G01N 2035/0415; G01N 2035/0484; G01N 2035/0486
See application file for complete search history.

(56) References Cited

U.S. PATENT DOCUMENTS
4,928,453 A * 5/1990 Ferkany ............ G01N 35/04
198/341.07
7,331,474 B2 2/2008 Veiner et al.
(Continued)

FOREIGN PATENT DOCUMENTS
CN 1932514 A 3/2007
CN 102221624 A 10/2011
(Continued)

OTHER PUBLICATIONS
Zhang et al (Yi Zhang, Susan Finger, Stephannie Behrens, "Introduction to Mechanisms", Rapid design through virtual and physical prototyping, Chapter 6, Carnegie Mellon University, https://www.cs.cmu.edu/~rapidproto/mechanisms/chpt6.html, published online Apr. 30, 2012.*

*Primary Examiner* — Benjamin R Whatley
(74) *Attorney, Agent, or Firm* — Kory D. Christensen

(57) ABSTRACT

A sample rack moving mechanism is provided for removing a sample rack loaded with one or more sample containers from a temporary storing section, and returning the sample rack loaded with the sample containers holding the tested sample to the temporary storing section. The sample rack moving mechanism may include a drive element, a cam driven by the drive element to rotate and having a curve contour, a cam follower moving following the outer contour of the cam, a guide groove corresponding to the temporary storing section, having a bottom plane of the same height as a support plane of the temporary storing section for supporting the sample rack, and capable of moving the sample rack, and a support element driven by the cam follower to move upward and downward and driving the sample rack to horizontally move between the temporary storing section and the guide groove.

20 Claims, 11 Drawing Sheets

(56) References Cited

U.S. PATENT DOCUMENTS

| | | | |
|---|---|---|---|
| 2010/0233754 A1 | 9/2010 | Guex | |
| 2011/0073438 A1* | 3/2011 | Takai | G01N 35/026 198/367 |
| 2015/0160249 A1* | 6/2015 | Bucher | G01N 35/026 422/65 |

FOREIGN PATENT DOCUMENTS

| | | |
|---|---|---|
| CN | 103364577 A | 10/2013 |
| CN | 203479815 U | 3/2014 |
| JP | H06-082565 U * | 11/1994 |

* cited by examiner

SAMPLE RACK MOVING MECHANISM, SAMPLE RACK CONVEYING DEVICE AND SAMPLE ANALYZING EQUIPMENT

CROSS REFERENCE

The present disclosure is a continuation of Patent Cooperation Treaty Application No. PCT/CN2014/075617, filed on Apr. 17, 2014, which is hereby incorporated by reference.

TECHNICAL FIELD

The present disclosure relates to medical equipments, and, to a sample rack moving mechanism for removing a sample rack that holds one or more collected sample containers containing a sample from a temporary holding position and returning it thereto, a sample rack conveying device for moving the removed sample rack to an analyzing and testing position and returning the sample rack that holds the sample container containing the tested samples to the temporary holding position, and a medical testing equipment including the sample rack moving mechanism, the sample rack conveying device and a device for analyzing and testing the conveyed samples, and also suitable in medical testing environment or other analyzing and testing environments.

BACKGROUND

Sample tubes are usually adopted to collect samples of blood and body fluid to be analyzed in medical equipments. The sample tubes are generally inserted into a sample rack, such that one sample rack can store a plurality of sample tubes, thus facilitating movement and storage of the sample tubes while improving testing efficiency. Many medical equipments adopt a combination of the sample rack and the sample tubes. The sample rack with the inserted sample tubes is directly conveyed into the equipments for sample analysis, thereby enabling simple and convenient operation of such equipments. Although various equipments have different ways of conveying the sample rack inside it, the purpose is to convey the sample rack by means of a moving shaft, such that each sample in the sample tube in the sample rack can be analyzed. It is required that, during the period of conveying, each sample tube can accurately reach the testing places without tilting, rolling or damaging.

At present, there are two main solutions of conveying the sample rack by the medical equipment: one is to move the sample rack up and down, and the other is to translate the sample rack in a guide groove. The latter solution requires the sample rack to move back and forth, where a positioning pin can be protruded to be inserted into a positioning hole in the sample rack and the sample rack can be driven to move by another shaft or other shafts. The translation solution requires a positioning hole disposed in the sample rack, and this leads to a high requirement on the location accuracy of the positioning hole. However, since manufacturing tolerance may affect the positioning accuracy of a moving shaft, the positioning pin, when being protruded, is likely to be pressed against the sample rack, rather than being successfully inserted into the positioning hole. In this case, the moving shaft may be stuck, or the sample rack may be tilted to cause splashed liquids.

Considering a power part of the moving shaft, a motor as a power source may be used to drive the moving mechanism when the medical equipments are electrically controlled. The motor can be a rotary motor, in which case rotary movement is required to be converted into linear movement. A motor which is capable of moving linearly may lead to a special structure, a high cost and a large size. On the other hand, the rotary motor requires an intermediate transmission mechanism, thus increasing equipment manufacturing cost and occupation space. Therefore, there are high design requirements on the structure of the intermediate mechanism, the size of the occupation space and the transmission accuracy.

SUMMARY

This disclosure provides a sample rack moving mechanism having a simple and compact structure, enabling accurate and reliable transmission, and capable of avoiding tilting of sample tubes and splashing of liquids.

In one aspect, a sample rack moving mechanism may be provided, where the sample rack moving mechanism may cooperate with a storing section loaded with one or more sample racks, and is capable of removing the sample racks loaded with one or more sample containers from a holding position on the storing section and/or returning the sample racks loaded with the one or more sample containers to the storing section. The sample rack moving mechanism may include a first drive element, a cam, a cam follower, a second drive element, a guide groove and a support element. The cam may include a curve contour and be driven by the first drive element. The cam follower may cooperate with the cam and follow along the curve contour of the cam. The guide groove may correspond to a position of the storing section, so as to move the sample racks from the holding position to the guide groove. Here, a length direction of the guide groove and a movement direction of the sample racks disposed on the storing section may be substantially along a same direction, and a bottom plane of the guide groove may be of a substantially same height as a support plane of the storing section for placing the sample racks. The support element may be fixed on the cam follower and driven by the cam follower to move upward and downward, so as to be detachably connected with the sample racks. The support element is capable of driving, through connection with the second drive element, the sample racks to substantially horizontally move between the storing section and the guide groove.

In another aspect, a sample rack conveying device may be provided. The sample rack conveying device may include a storing section, the above-described sample rack moving mechanism and a conveying member, where the conveying member is capable of conveying the guide groove and one of the sample racks on the guide groove along a direction substantially perpendicular to the length direction of the guide groove.

In yet another aspect, a sample analyzing equipment can be provided, where the sample analyzing equipment can include the above-described sample conveying device.

BRIEF DESCRIPTION OF DRAWINGS

In order to more clearly describe technical solutions according to embodiments of the present disclosure, accompanying drawings used in the embodiments will be briefly introduced hereinafter. Apparently, the accompanying drawings described hereinafter should be substantially considered to be illustrative, not limitative, and are merely expressions of the embodiments and examples of the present disclosure. Persons skilled in the art may also derive other different embodiments from these accompanying drawings without creative efforts.

DETAILED DESCRIPTION

The present disclosure is further described in detail hereinafter with reference to the accompanying drawings and embodiments, in order to more fully understand the purposes, technical solutions and advantages of the present disclosure. It should be understood that, the embodiments described herein are merely for explaining the present disclosure, not limiting it.

It should be noted that, the term "sample" used in the present application, refers to any sample of body fluid and blood which can be contained in sample tubes to be analyzed. The sample includes, but is not limited to, materials (including biological materials collected on swabs from such as throat, vagina, cartilage, rectum, urethra, nose or nasopharynx swabs), fluid, urine, blood, saliva, serum, plasma, feces, inspiration, washing liquor, tissue homogenate and treatment solution.

When an element is "connected", "fixed" or "disposed" as stated to another element, it may be connected, fixed or disposed to another element directly or via an intermediate element.

It should be further noted that, direction terminologies, such as "left", "right", "upper", "lower", "transverse", "longitudinal" and the like, are merely concepts relative to each other, or are referred to under normal using state of products, and thus should not be considered to be limitative.

Figure 1:
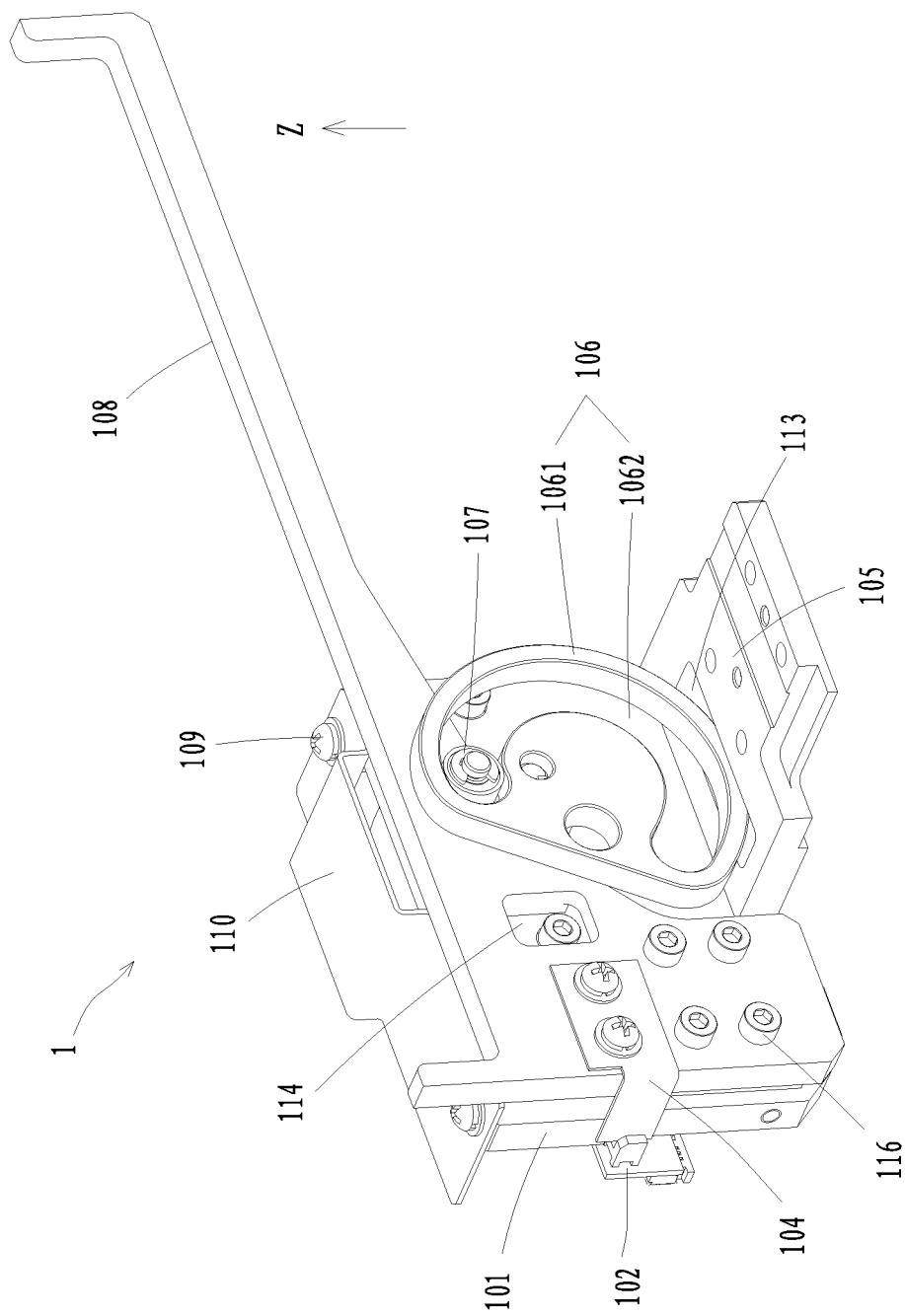
FIG. 1 is a schematic assembly diagram for a combination structure of a cam and a support element according to an embodiment of a sample rack moving mechanism of the present disclosure.
Figure 2:
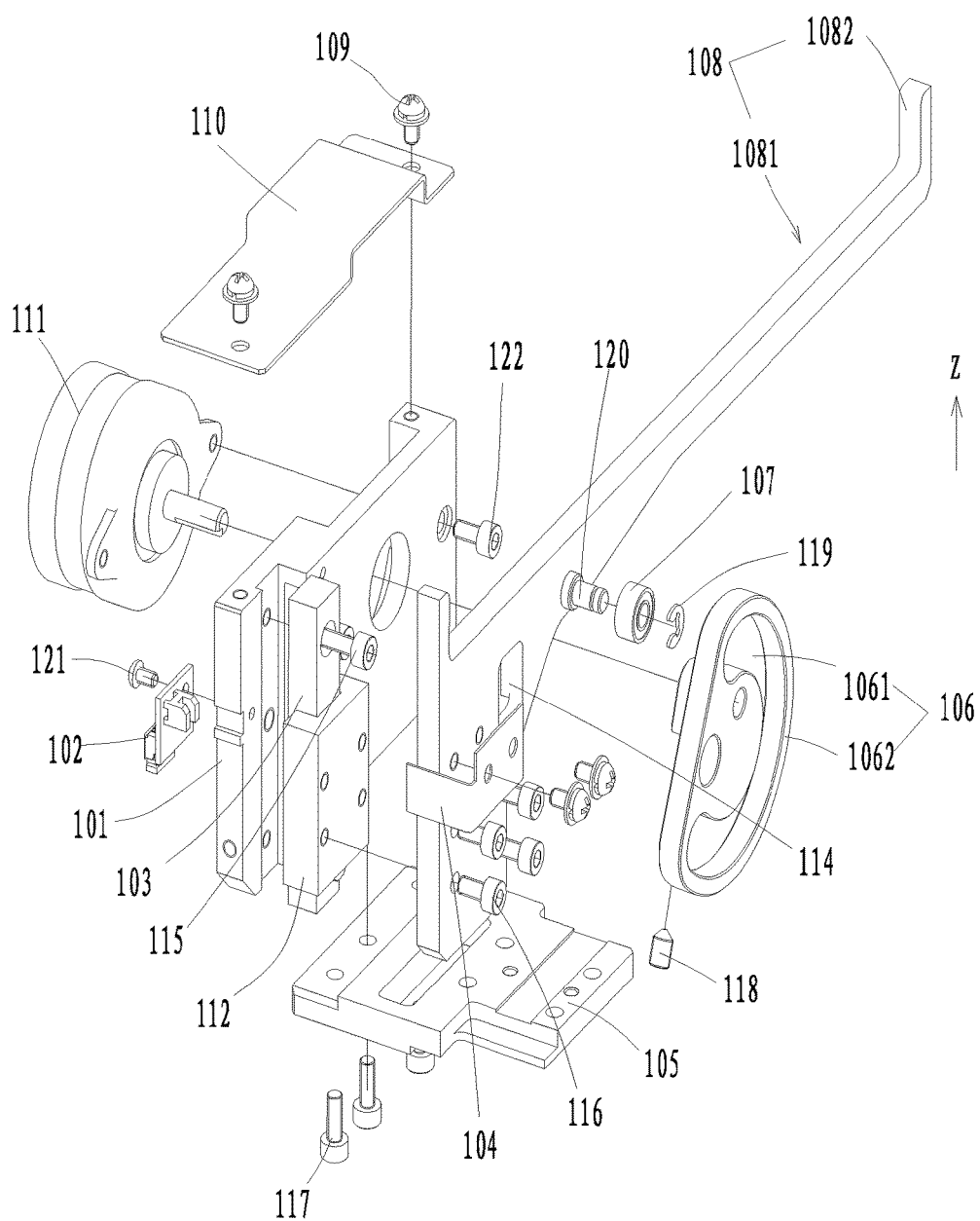
FIG. 2 is an exploded diagram for a combination structure of a cam and a support element according to an embodiment of a sample rack moving mechanism of the present disclosure.

As shown in FIG. 1 to FIG. 9, a sample rack moving mechanism according to an embodiment of the present application may be disposed to cooperate with a temporary storing section 2 loaded with one or more sample racks 5, where one or more sample tubes that contain(s) sample(s) for testing may be arranged on each sample rack 5. The sample rack moving mechanism may be used for removing the sample rack 5 from a temporary holding position on the temporary storing section 2, and returning the sample rack 5 in which the sample(s) have/has been subjected to a test in a testing position to the temporary storing section 2. The sample rack moving mechanism may include a vertical movement member 1 as shown in FIG. 1 to FIG. 2 (moving along a Z-axis direction as shown in Figs.) and a longitudinal movement member 3 (moving along a Y-axis direction as shown in Figs.). The vertical movement member 1 may include a combination of a cam and a support element, where the vertical movement may include a base 105, a first drive element, the cam 106, a cam follower 107, and the support element 108. The base 105 may be fixable on a worktable (not shown), and may be used for supporting and mounting respective members. The first drive element may be a first rotary motor 111. The cam 106, which can be provided with a preset curve contour, may be fixedly connected with the first rotary motor 111 and driven by the first rotary motor 111 to rotate. The cam follower 107 may cooperate with the cam 106 and move following the curve contour of the cam 106. The support element 108 may be fixedly connected to the cam follower 107, and the support element 108 can be driven by the first rotary motor 111 to move upward and downward (in the Z-axis direction as shown in Figs.), so as to be detachably connected with or detached from the sample rack 5 following the movement of the cam follower 107 along the contour track of the cam 106. The longitudinal movement member 3 may include a second drive element 301 and a movable guide groove 308, and operate for moving the sample rack 5 from the temporary holding position to the guide groove 308. The guide groove 308 may be disposed corresponding to the temporary storing section 2, where the guide groove may be parallel with each grid of the temporary storing section 2. A length direction of the guide groove 308 and a movement direction of the sample rack 5 on the temporary storing section 2 are substantially along a same direction (substantially along a same line for instance), and a bottom plane of the guide groove 308 is of the substantially same height as a support plane of the temporary storing section 2 for placing the sample rack 5 (i.e., the bottom plane and the support plane are located on a substantially same horizontal plane), thus facilitating moving the sample rack 5 from the temporary holding position to the guide groove 308. Furthermore, the support element 108 may be connected to the second drive element 301. In this way, the support element 108 may be first driven by the second drive element 301 to move longitudinally (the Y-axis direction as shown in Figs.) from the guide groove 308 to a bottom of the sample rack 5 to be moved on the temporary storing section 2. Then, the support element 108 may be moved upward (the Z-axis direction) by means of the rotation of the cam 106, such that the support element 108 may be detachably connected to the sample rack 5. Then, the support element 108 may be driven, by means of a reverse operation of the second drive element 301, for removing the sample rack 5 from the temporary storing section 2 and for returning the sample rack 5 to the guide groove 308. Correspondingly, after the sample within the sample tube on the sample rack 5 is tested, the support element 108 may be driven by the second drive element 301 to move the sample rack 5 longitudinally and to return the sample rack 5 to a designated position on the temporary storing section 2. Then, the support element 108 may be detached from the sample rack 5 by means of the cooperation of the first rotary motor 111, the cam 106 and the cam follower 107.

Compared to other mechanism converting rotary movement into linear movement, cam transmission is adopted by the aforementioned sample rack moving mechanism according to the present disclosure. In this way, the sample rack moving mechanism can have a simple, small and compact structure to be used in those equipments having small internal space, and it can be advantageous to cooperate and arrange the sample rack moving mechanism with other relating mechanisms. Moreover, the vertical movement of the support element 108 depends on the curve contour of the cam 106, such that an intermittent movement of the support element 108 can be realized during the process of moving the sample rack 5, and there can be good movement reliability to meet functional requirements. Also, an output shaft of the first rotary motor 111 may be directly connected with the cam 106 without other intermediate elements to provide rotary actuation, and the rotary motor can be low in cost, convenient in commercial availability and good in universality. Furthermore, since the cam transmission of the cam 106 has a high transmission accuracy, the support element 108 may be conveniently and accurately located at the bottom of the sample rack 5, such that the support element 108 may be easily designed according to the structure of the sample rack 5 and the support element 108 can be ensured to have good contact with the sample rack 5 to achieve the moving and supporting functions. On the other hand, the guide groove 308 can be disposed oppositely to the temporary storing section 2, such that the length direction of the guide groove 308 and the movement direction of the sample rack 5 in the temporary storing section 2 are substantially along a same line, and the bottom plane of the guide groove 308 is of the substantially same height as the support plane of the temporary storing section 2 for supporting the sample rack 5. Accordingly, it can be ensured that the movement of the sample rack 5, when removing from or returning to the temporary storing section 2, is substantially along the same line and on the same horizontal plane, such that the sample rack can be prevented from stucking or tipping to avoid splashing of the samples during the moving process.

Figure 3:
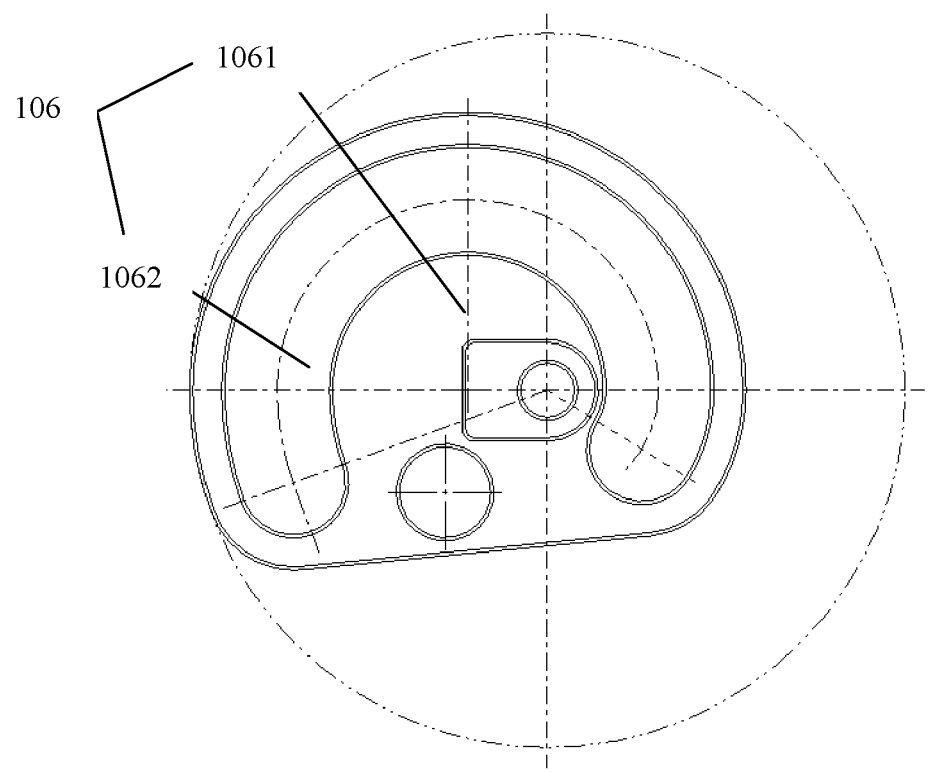
FIG. 3 is a schematic view for a cam of a sample rack moving mechanism according to an embodiment of the present disclosure.
Figure 4:
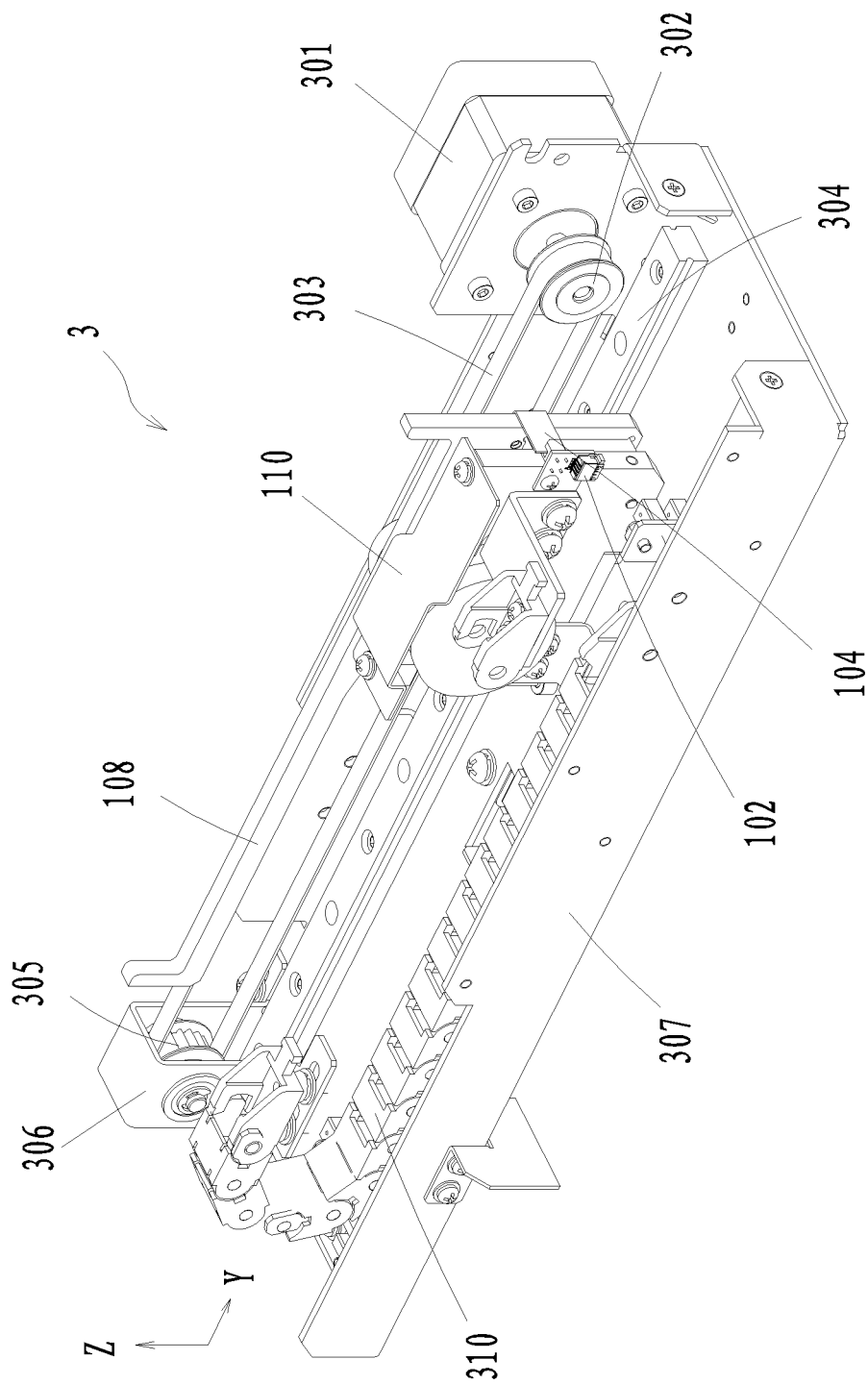
FIG. 4 is a first schematic structural diagram for a sample rack moving mechanism of the present disclosure.
Figure 5:
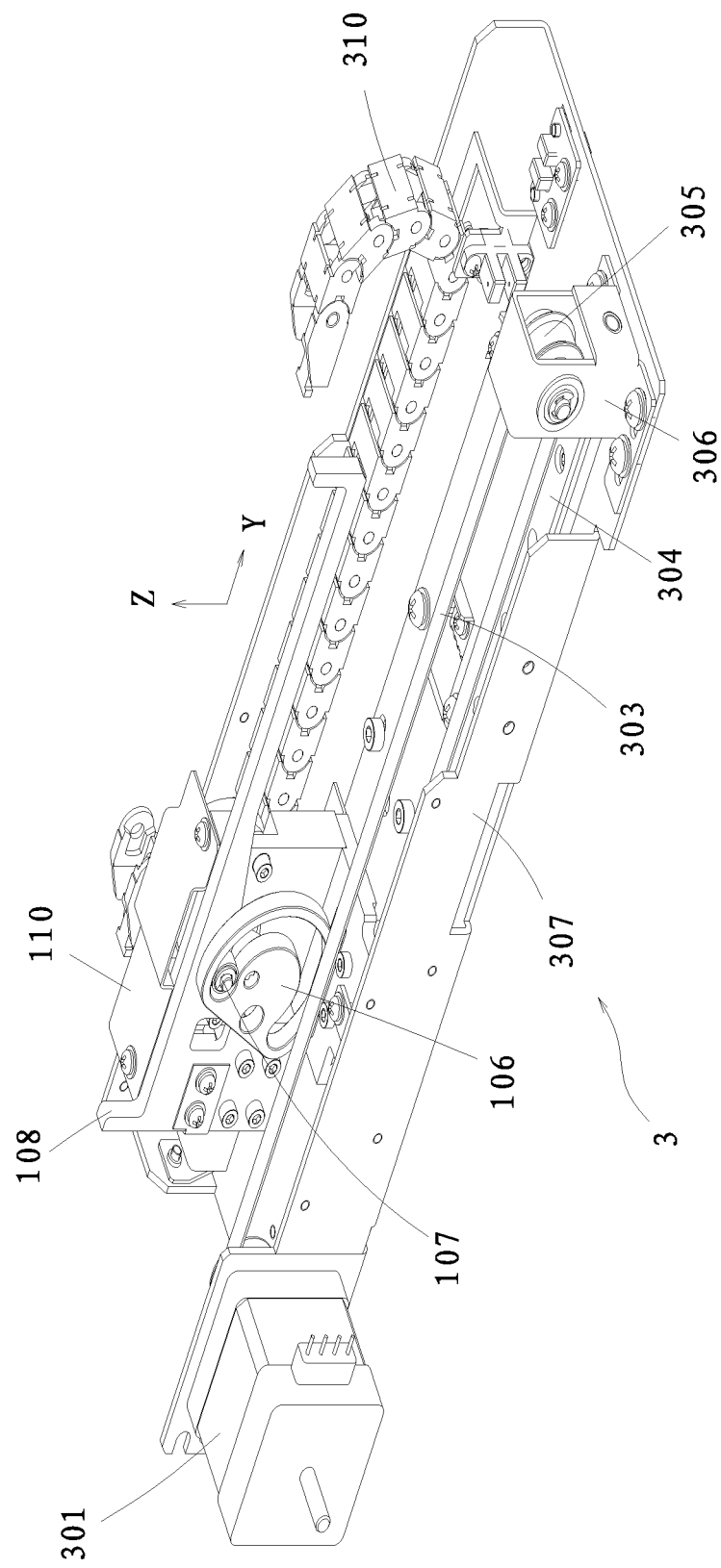
FIG. 5 is a second schematic structural diagram for a sample rack moving mechanism of the present disclosure.

Referring to FIG. 1 to FIG. 3, in an embodiment of the present disclosure, the cam 106 may include a main body 1061 which may be a disk-shaped component surrounding the output shaft of the first rotary motor 111 and have a fixation position deviating from a rotary center of the cam 106 (i.e., eccentrically disposed on the output shaft of the first rotary motor 111). The main body 1061 may include a cam groove 1062, where according to the movement of the support element 108, the cam groove 1062 may be provided with a nearest dwell angle for locating the support element 108 at the bottom (a lower position) of the sample rack 5, a push-travel motion angle for causing the support element 108 to move upward so as to be detachably connected with the sample rack 5 and a farthest dwell angle for locating the support element 108 at a highest position to be connected with the sample rack 5. The support element 108 may be provided with a pin shaft 120 protruding outward. The cam follower 107 may be an annular roller surrounding the pin shaft 120, and may be inserted and fixed within the cam groove 1062 by a snap ring 119. The snap ring 119 may block the cam follower 107 to prevent the cam follower 107 from falling and facilitate the replacement of the cam follower 107 when it is worn. In this way, when the cam 106 is driven by the first rotary motor 111 to rotate, the cam follower 107 can be enabled to slide in the cam groove 1062, so as to drive the support element 108 to move upward and downward.

Further referring to FIG. 3, the main body 1061 can have a kidney-shaped outer contour, and a center of the kidney-shaped structure may deviate from the rotary center of the cam. The cam groove 1062 may be an arc-shaped groove penetrating through the disk-shaped cam, where the cam groove 1062 may be disposed adjacent to the outer contour of the cam and a curvature of the cam groove is substantially the same as that of the outer contour of the cam. Such structure may ensure the motion stability of the cam 106 during its movement, and regular shape design is advantageous for manufacture processing to ensure manufacture accuracy. Also, when the cam groove 1062 is provided adjacent to the outer contour of the main body 1061 and the curvature of the cam groove is substantially the same as that of the outer contour, the cam groove 1062 can be provided with a longer motion curve, thus not only enabling a smaller and more compact cam 106 but also facilitating processing and cost reducing.

It can be understood that, the cam 106 is not limited to the aforementioned disc-shaped or kidney-shaped structure, while the cam groove is also not limited to the arc-shaped groove structure. Alternatively, a moving cam, a cylindrical cam or other cam structure may also be adopted, and a spring may enable the support element 108 to return.

Referring to FIG. 2 again, the first rotary motor 111 may be fixed on a first mounting plate 101. The first mounting plate 101 may be vertically disposed and fixed on the base 105 by a screw 117. The first rotary motor 111 may be fixed on one side of the first mounting plate 101 by a screw 122, and a top of the first rotary motor 111 may be covered by a first protective cover 110. The first protective cover 110 may be fixed on the top of the first mounting plate 101 by a screw 109, so as to prevent damages to the first rotary motor 111 due to liquid splashing on the first rotary motor 111 when the sample rack 5 is moving. The support element 108 and the cam 106 can be located on another side of the first mounting plate 101 opposite to the first rotary motor 111. A through hole may be provided on the first mounting plate 101. The output shaft of the first rotary motor 111 may pass through this through hole, and a V-shaped groove may be disposed on the output shaft in a radial orientation. The main body 1061 of the cam may be fixed to the output shaft of the first rotary motor 111 by a set screw 118, and can be driven by the first rotary motor 111 to rotate. A first guide rail 103 may be further disposed on the first mounting plate 101 facing the support element 108, where the first guide rail 103 can be fixed by a screw 115. Accordingly, a slide block 112 capable of cooperating with the first guide rail 103 to slide may be correspondingly disposed on a surface of the support element 108 facing the first guide rail 103, where the slide block may be fixed to the support element 108 by a screw 116. In this way, the support element 108 may be driven by the cam follower 107 to move upward and downward along the first guide rail 103 through the cooperation between the first guide rail 103 and the slide block 112.

It can be understood that, the cooperation of the first guide rail 103 and the slide block 112 may be designed in some other ways. The first guide rail 103 may be integrally formed with the first mounting plate 101. Alternatively, as shown in FIG. 2, a mounting groove may be provided on the first mounting plate 101. The first guide rail 103 may be embedded and fixed in the mounting groove, so as to ensure the mounting accuracy of the first guide rail 103, while reducing the weight of the first mounting plate 101. Similarly, the slide block 112 may be integrally formed with the support element 108. Alternatively, a slide slot may be disposed on the first mounting plate 101, while a slider cooperating with the slide slot may protrude from the support element 108. Furthermore, linear bearings may be adopted in other example, which are not discussed herein.

In order to reduce the weight of the whole sample rack moving mechanism, as shown in FIG. 1, an interference avoiding groove 113 may be provided on the base 105 corresponding to the bottom of the cam 106 according to a swing arc of the cam 106, so as to reduce the weight of the base 105 and reduce an overall mounting height of the support element 108. Similarly, a through slot 114 may be provided in the mounting position of the screw 115 on the support element 108, thus not only facilitating mounting the first guide rail 103, but also enabling the support element 108 to be more adjacent to the first mounting plate 101 so as to reduce the space between the first guide rail 103 and the slide block 112 and make the whole structure be more compact.

Referring to FIG. 4 to FIG. 9, the second drive element 301 may be a second rotary motor fixed at one end of a support base 307 in an embodiment of the present disclosure. The support base 307 may be used for supporting the whole vertical movement member 1 and the longitudinal movement member 3. The guide groove 308 may be connected with the support base 307 via a second protective cover 309, where the guide groove 308 may be located above the support base 307. The vertical movement member 1 may be disposed within a space enclosed by the second protective cover 309, thus preventing liquid and foreign objects from contaminating the movement members. A first driving wheel 302 may be disposed on the output shaft of the second rotary motor, and a first driven wheel 305 may be disposed corresponding to the first driving wheel 302, where the first driven wheel 305 can be fixed at another end of the support base 307 via a first fixation base 306. A first transmission belt 303 may be connected between the first driving wheel 302 and the first driven wheel 305. A second guide rail 304 can be disposed in parallel with a transmission direction of the first transmission belt 303. A length direction of the second guide rail 304 may be substantially the same as the movement direction of the sample rack 5 on the temporary storing section 2. One end of the base 105 of the vertical movement member 1 may be connected with the first transmission belt 303, while another end of the base may be slidably disposed on the second guide rail 304. In this way, the vertical movement member 1 may be driven by the second drive element 301 to move longitudinally (the Y-axis direction) along the second guide rail 304 through the guidance of the second guide rail 304 and the movement of the first transmission belt 303, such that the sample rack 5 may be driven by the support element 108 to move between the temporary storing section 2 and the guide groove 308.

In the aforementioned structure, the first transmission belt 303 may be a synchronous belt, and may further be provided with a drag chain 310. Accordingly, the first transmission belt can have accurate and reliable transmission, a small load, a compact structure, and high transmission efficiency.

It can be understood that, the second drive element 301 may also be a linear cylinder, and the sample rack 5 may also be driven to move between the temporary storing section 2 and the guide groove 308 by connecting the support element 108 with a piston rod of the cylinder. However, such a structure has a higher cost compared to the mode of transmission by a synchronous belt, and its movement distance is also readily restricted. Alternatively, a combination of a nut and a lead screw may be adopted for transmission. The support element 108 can be connected with the nut. The sample rack may be moved by rotating the lead screw relatively to the nut to drive the support element 108 to move. Moreover, the aforementioned functions may also be realized by a linear bearing. Thus, all those structures should fall within the protection scope of the present disclosure, as long as they can enable that the sample rack 5 may be driven by the support element 108 to move between the temporary storing section 2 and the guide grooves 308.

Please referring to FIG. 1 to FIG. 2 again, the support element 108 in an embodiment of the present disclosure can be a fork 108 with an opening 1081, where the opening 1081 may be provided with a supporting surface. The support element 108 may be driven by the cam 106 and the cam follower 107 to move to the bottom and/or two sides of the sample rack 5, and raised (the Z-axis direction as shown in Figs.) after being horizontally positioned, so as to be connected with and support the sample rack 5. In this embodiment, the sample rack 5 may be held by the fork, where a bottom surface of the fork can be located at a substantially same height as the support plane of the temporary storing section 2 for supporting the sample rack 5, and claws 1082 at both ends of the fork may be used to push the sample rack 5, such that the sample rack 5 can move back and forth between the temporary storing section 2 and the guide groove 308. The fork 108 can be higher than other members of the vertical movement member 1 after being raised, thus avoiding a larger space requirement compared to other linear moving mechanisms in which the movement members need to be supported at both ends. A size of the opening 1081 can match a bottom size of the sample rack 5, or can be greater than the sample rack 5 (when the sample rack 5 and the fork 108 are aligned centrally, a distance between the claws 1082 and a contact surface of the sample rack 5 may be set to be about 2.5 MM). In this way, the fork 108 may readily receive the sample rack 5, thus avoiding positioning inaccurately, failing to receive the sample rack 5 or tipping the sample rack 5 by the fork 108, and having a high reliability and a very simple structure.

It can be understood that, the structure enabling to position the support element 108 relative to the sample rack 5 and to support the sample rack 5 using the support element 108 is not limited to the fork or the illustrated structure. All those structures should fall within the protection scope of the present disclosure, as long as they can enable that the sample rack 5 may be supported and driven to move horizontally.

Please referring to FIG. 1 to FIG. 2 again, an optical coupler 102 can be further disposed on the first mounting plate 101. A through slot can be disposed in the optical coupler 102; for instance, the through slot may be perpendicularly arranged relative to the optical coupler. Here, a groove may be provided on the first mounting plate 101, and the optical coupler 102 can be positioned and fixed in the groove by a screw 121, so as to ensure the mounting accuracy of the optical coupler 102. A light blocking plate 104 capable of cooperating with the optical coupler 102 may be disposed on the support element 108 correspondingly. When the support element 108 moves upward or downward, an isolation signal can be produced when the light blocking plate 104 passes through the through slot of the optical coupler 102, and the first rotary motor 111 may be controlled, by transmitting the isolation signal to a drive circuit, to be turned on or off and in turn to control the rotation of the cam 106, so as to raise or lower the support element 108. The first rotary motor 111, the first guide rail 103 and the light blocking plate 104 can all be mounted on the first mounting plate 101, thereby guaranteeing the relative mounting accuracy of those members and a simple structure.

Referring to FIG. 6 to FIG. 9, the present disclosure further provides a sample rack conveying device capable of conveying the guide groove 308 on the sample rack moving mechanism and the sample rack 5 in this guide groove 308 to a target testing position. The sample rack conveying device can include the temporary storing section 2, the aforementioned sample rack moving mechanism and a transverse conveying member 4, where the transverse conveying member is capable of driving the whole sample rack moving mechanism to move. By means of the transverse conveying member 4, after the sample rack 308 has been separated from the temporary storing section 2 and located in the guide groove 308, the sample rack 308 holding the sample to be tested may be conveyed, together with the guide groove 308, to a testing platform (i.e., be conveyed to the target testing position along an X-axis direction as shown in Figs.), or the sample rack 5 on which the sample has been tested can be conveyed from the testing platform to an initial position where the sample rack moving mechanism begins moving transversely, and then be moved by the sample rack moving mechanism from the guide groove 308 to the temporary storing section 2. The initial position can be a position where the sample rack 5 is moved from the temporary holding position on the temporary storing section 2 to the guide groove 308; the initial position can also be a beginning position from which the transverse conveying member 4 begins driving the guide groove 308 and the sample rack 5 to move to the target testing position, or a position where the transverse conveying member 4 stops moving after returning from the target testing position. Using the aforementioned structure, a conveying distance of the sample rack 5 is enabled to become longer, thus being advantageous for switching of different test platforms.

In an embodiment of a sample rack conveying device of the present disclosure, the transverse conveying member 4 can include a third drive element 402 and a third guide rail 405. The third drive element 402 may be a third rotary motor fixed on the worktable via a second mounting plate 401. A second driving wheel 403 may be connected with an output shaft of the third rotary motor, and a second driven wheel 406 may be disposed along a length direction of the third guide rail 405. The second driven wheel 406 may be fixed on the worktable via a second fixation base 407. A second transmission belt 404 may be connected between the second driving wheel 403 and the second driven wheel 406. The support base 307 on the sample rack moving mechanism may be slidably disposed on the third guide rail 405, and may be connected with the second transmission belt 404. In this way, the whole sample rack moving mechanism may be driven by the third drive element 402 to move along the length direction of the third guide rail 405 (i.e., along the X-axis direction as shown in Figs., or along a direction substantially perpendicular to the length direction of the guide groove) through the movement of the second transmission belt 404, such that the guide groove 5 along with the sample rack 5 on the guide groove 308 are enabled to be conveyed to the testing platform to convey the samples to the testing position, and to return after the sample testing is completed. Similarly, in the aforementioned structure, the second transmission belt 404 may be a synchronous belt provided with a drag chain 411. Accordingly, the second transmission belt can have accurate and reliable transmission, small load, a compact structure and high transmission efficiency.

It can be understood that, the third drive element 402 may be a combination of a nut and a lead screw for transmission. The support base 307 can be connected to the nut, and the sample rack moving mechanism can be driven to move through rotating the lead screw relative to the nut. Moreover, the aforementioned functions may also be realized by adopting linear bearing, which is not described herein.

Figure 6:
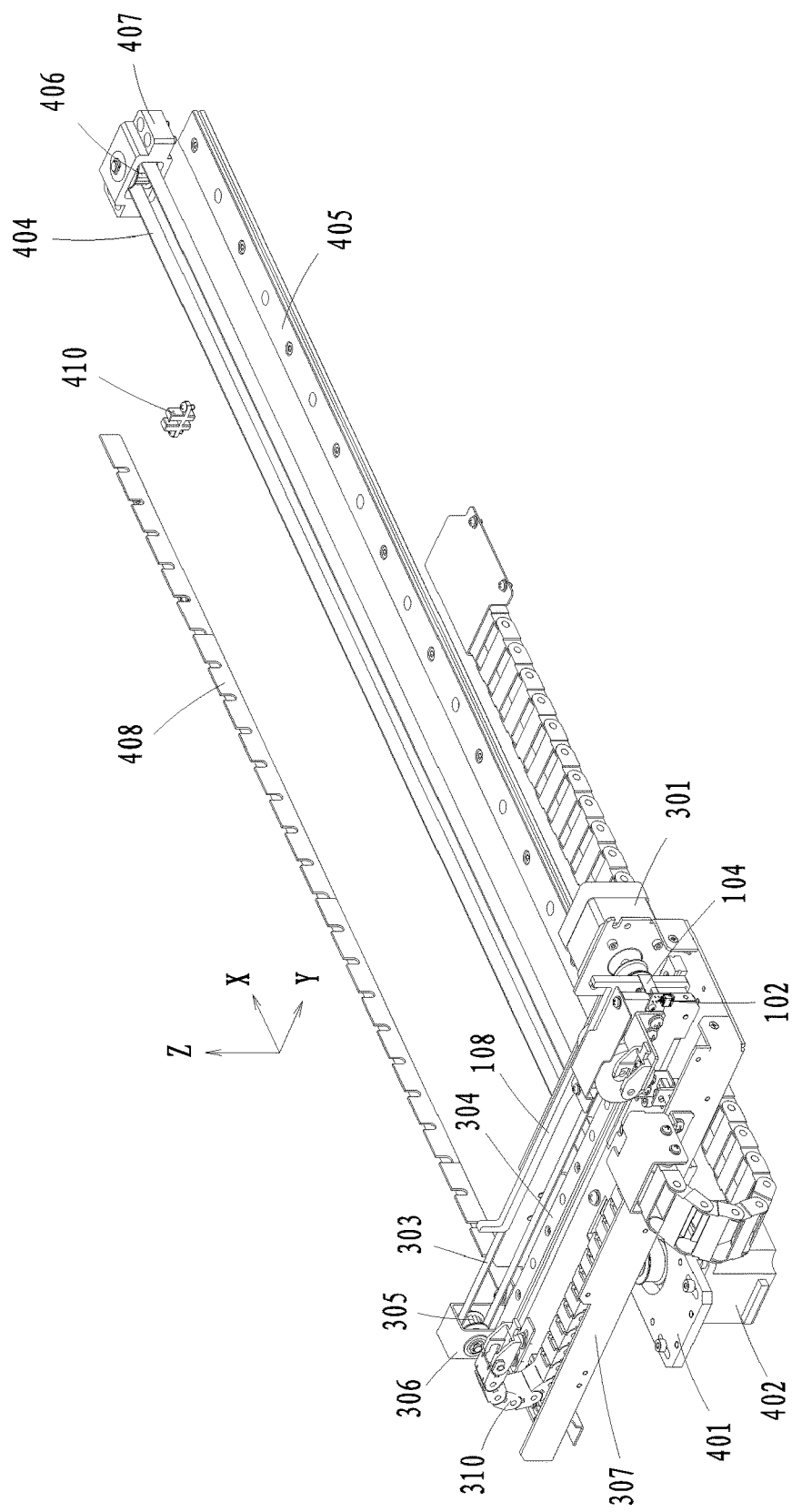
FIG. 6 is a first schematic structural diagram for a sample rack conveying device according to an embodiment of the present disclosure.
Figure 7:
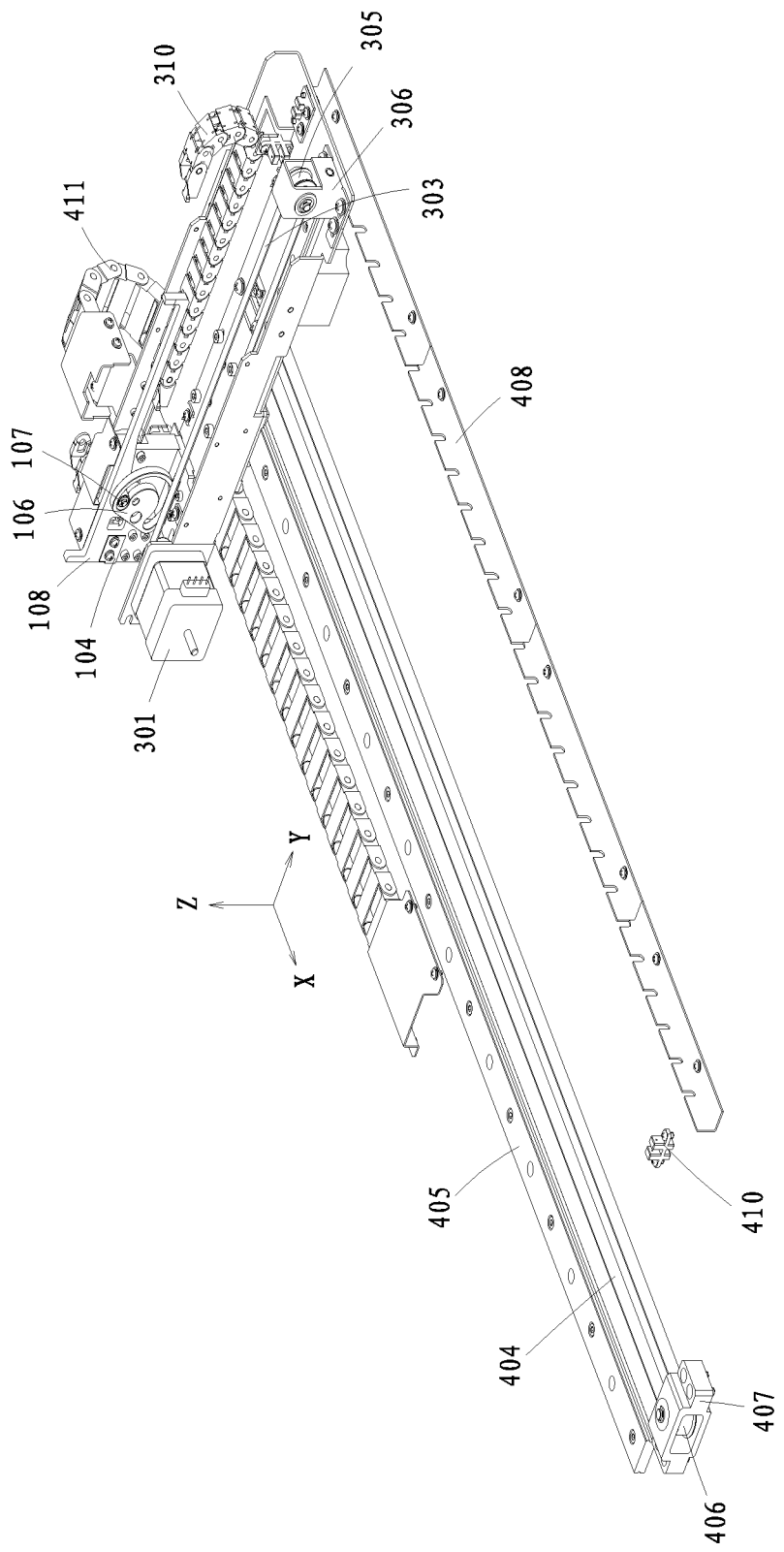
FIG. 7 is a second schematic structural diagram for a sample rack conveying device according to an embodiment of the present disclosure.
Figure 8:
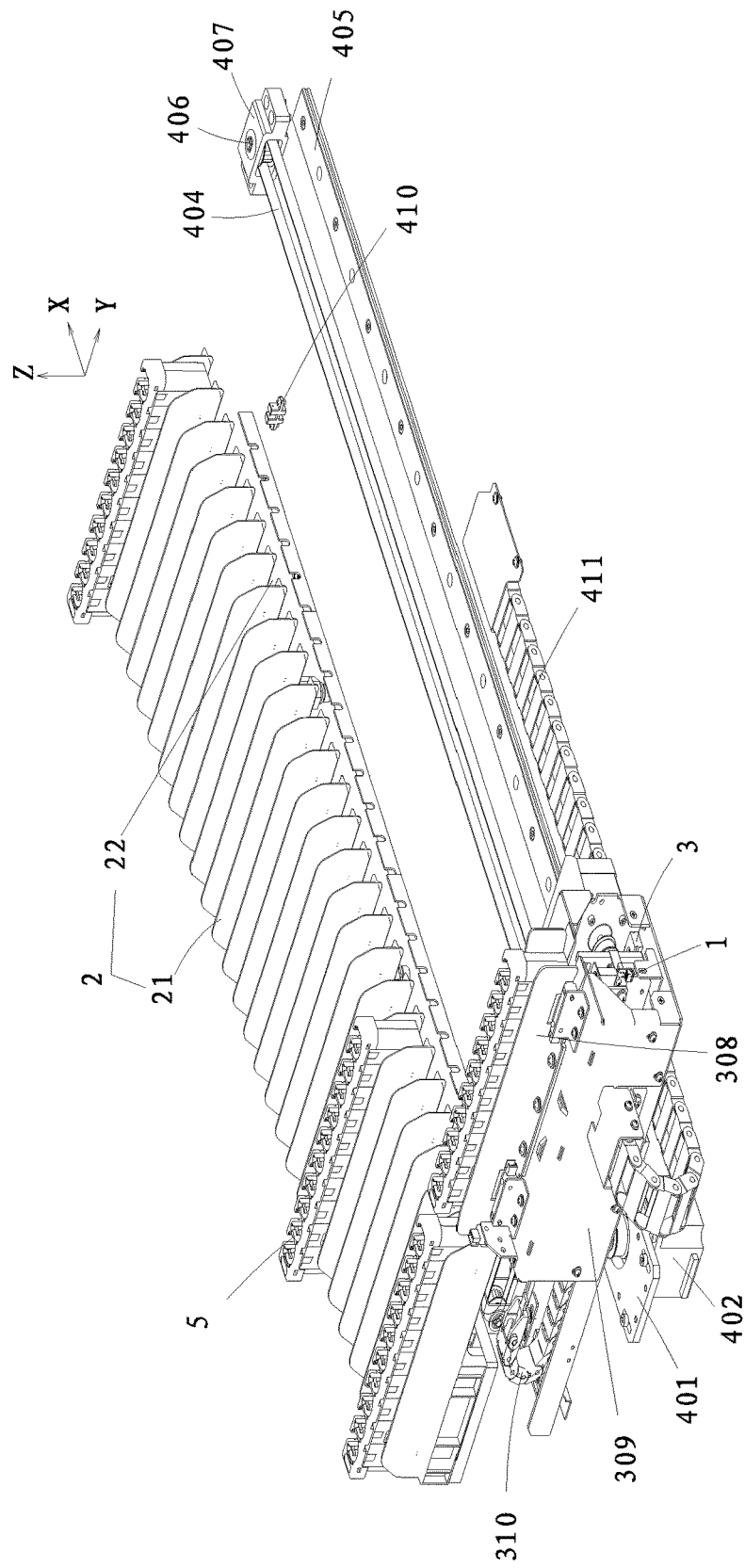
FIG. 8 is a third schematic structural diagram for a sample rack conveying device according to an embodiment of the present disclosure.

Please Referring to FIG. 6 to FIG. 9 again, the temporary storing section 2 may be designed according to the arrangement of the sample rack conveying device and the traverse conveying member 4, where the position where the sample rack 5 is located should facilitate the movement and the connection with the support element 108. Referring specifically to FIG. 8, the temporary storing section 2 may be driven by a drive piece to move, and can be provided with a plurality of grids 21 arranged in parallel along its movement direction. In each grid 21, one sample rack 5 can be disposed. Each sample rack 5 may be loaded with one or more sample tubes. A length direction of each grid 21 can be substantially the same as the longitudinal movement direction of the sample rack 5, and a width of each grid can match that of the guide groove 308, such that a movement center of the sample rack 5, a symmetrical center in the length direction of the grid 21 and a symmetrical center in the length direction of the guide groove 308 can be substantially along a same line, thus not only being advantageous for the movement of the sample rack 5, but also facilitating alignment of each grid 21 with the guide groove 308 after being moved. Referring further to FIG. 8, in an embodiment of the present disclosure, a through slot 22 may be provided on a bottom plane of each grid 21 for placing the sample rack 5. The through slot 22 may facilitate the insertion of the support element 108 (especially the opening 1081). After the support element 108 is connected and fixed to the sample rack 5, the opening 1081 may move along the through slot 22, which not only avoids the interference of the grid 21 with the support element 108, but also has a guiding effect when moving.

Figure 9:
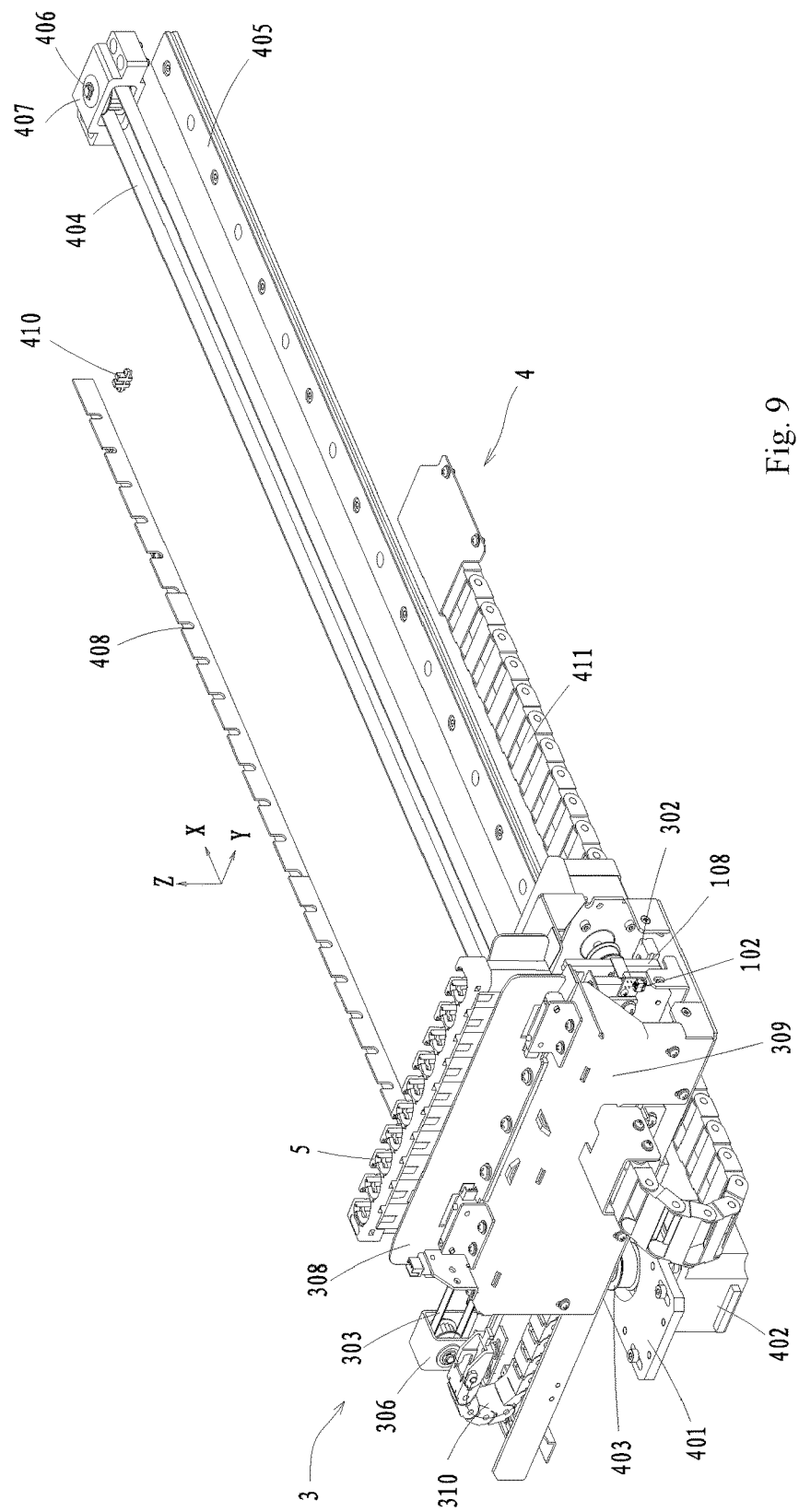
FIG. 9 is a fourth schematic structural diagram for a sample rack conveying device according to an embodiment of the present disclosure.

Referring to FIG. 7 to FIG. 9, in an embodiment of the sample rack conveying device of the present disclosure, a gear rack 408 may be disposed on one side of the temporary storing section 2 along the transverse direction (i.e., the direction substantially perpendicular to the length direction of the guide groove or each grid). The gear rack 408 may be provided with one or more tooth slots, where an amount of the tooth slot may correspond to that of the grids 21, i.e., the amount of the tooth slot may correspond to that of the sample racks 5 arranged on the temporary storing section 2 along the transverse direction(i.e., the direction substantially perpendicular to the length direction of the guide groove or each grid). A sensor may be disposed at a tail end of the gear rack 408. The sensor 410 may provide a sensing signal, such that the temporary storing section 2 may be moved forward and the sample rack conveying device may perform next action.

The operating process of the sample rack conveying device of the present disclosure is described hereinafter.

Figure 10A:
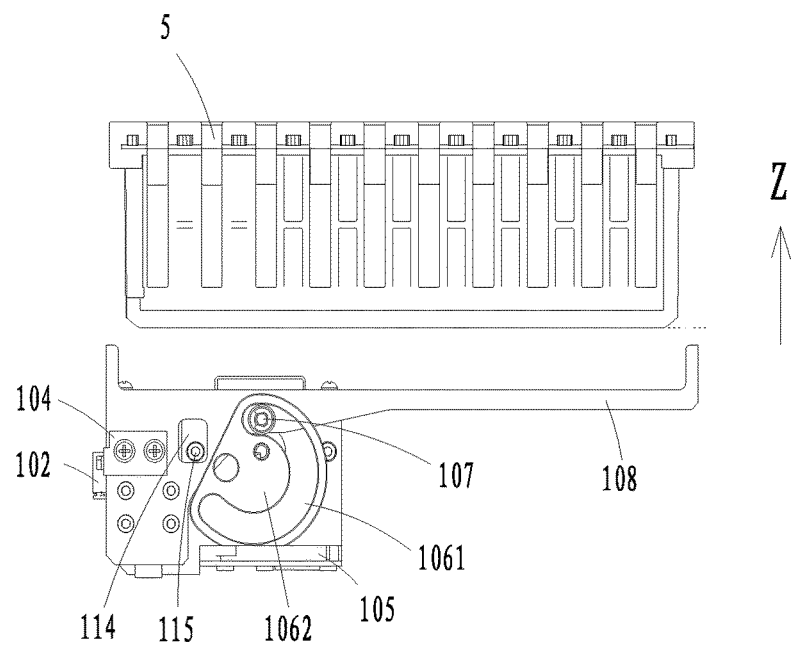
FIG. 10A is a schematic view illustrating when a support element of a sample rack conveying device is at a low location according to the present disclosure.
Figure 10B:
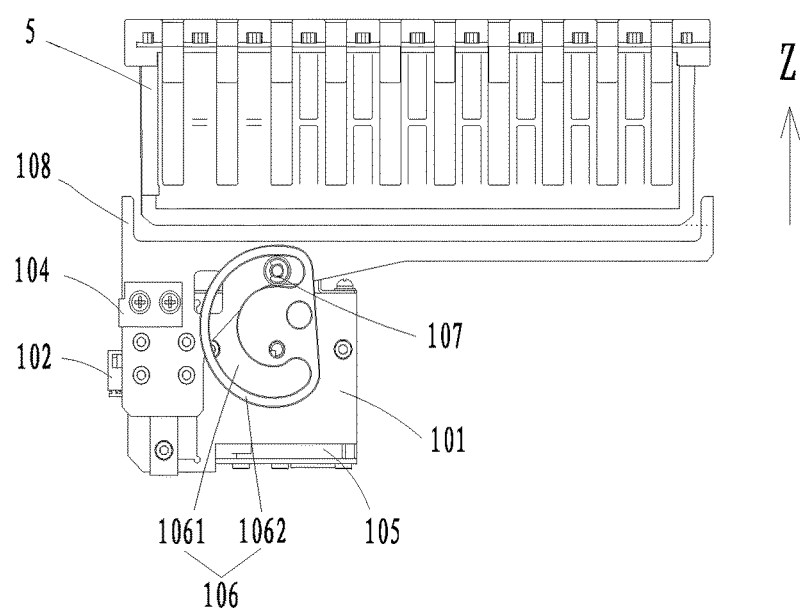
FIG. 10B is a schematic view illustrating when a support element of a sample rack conveying device is at a high location according to the present disclosure.
Figure 11A:
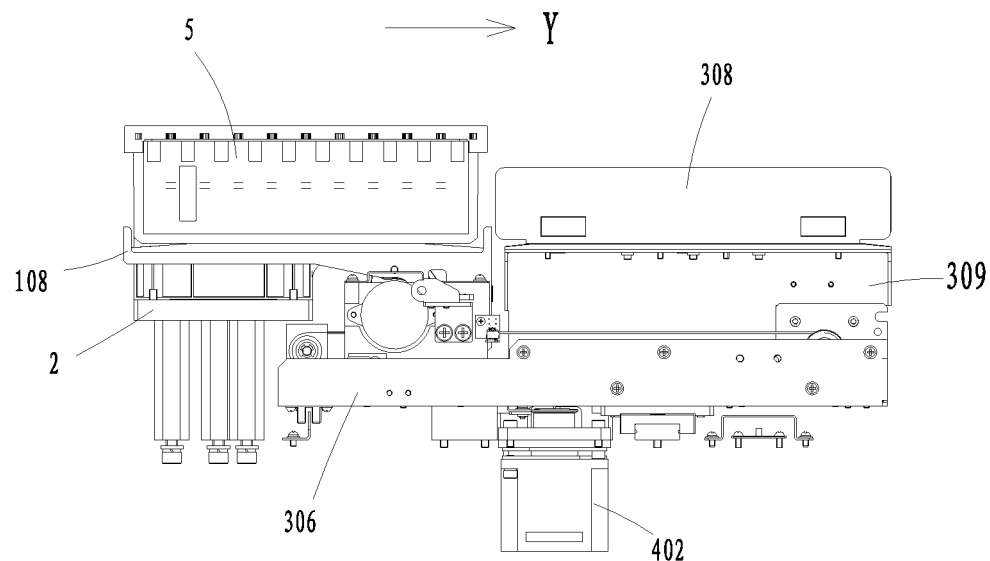
FIG. 11A is a schematic view illustrating when a support element of a sample rack conveying device is located at a temporary storing section according to the present disclosure.
Figure 11B:
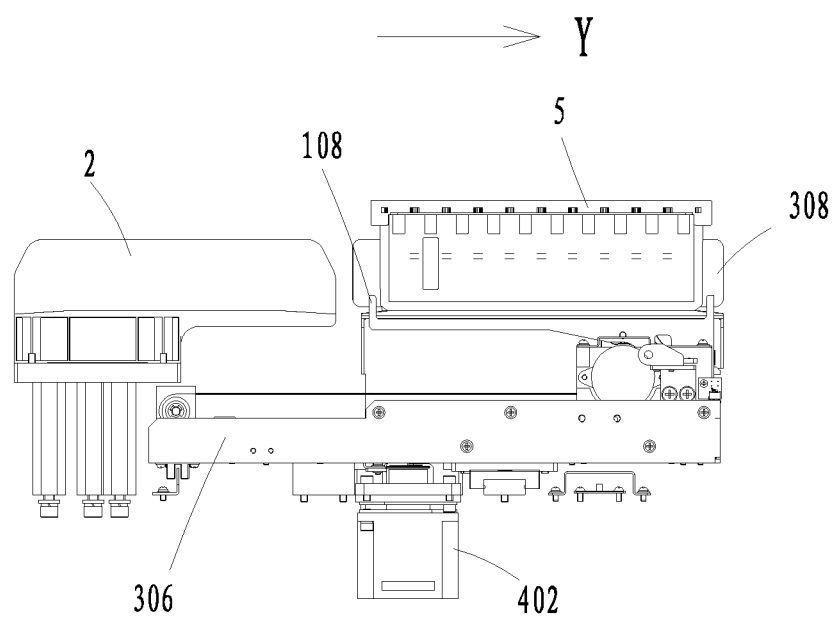
FIG. 11B is a schematic view illustrating when a support element of a sample rack conveying device is located at a guide groove according to the present disclosure.

Referring to FIG. 10 to FIG. 11, the sample tube holding the sample to be tested is located in the temporary storing section 2 before being conveyed. At this time, a control system may send signals such that the second drive element 301 is started to drive the first driving wheel 302 to rotate, and the first transmission belt 303 is driven by the driven wheel 305 to move while driving the base 105 and the vertical movement member 1 mounted on the base 105 to move along the second guide rail 304 (the Y-axis direction) in a movement direction oriented toward the temporary storing section 2. When the support element 108 moves to correspond to the bottom of the sample rack 5, the support element 108 is at a low location with the highest part thereof to be lower than the support plane of the sample rack 5 on the temporary storing section 2 (as shown in FIG. 10A), and the support element does not contact the sample rack 5. At this time, the optical coupler is triggered by the light blocking plate 104 passing through the through slot of the optical coupler 102. The second drive element 301 may stop rotating while the first rotary motor 111 (the first driving element) may be started to rotate the cam 106, such that the cam groove 1062 pushes the cam follower 107 to raise the support element 108 upward along the Z-axis direction. The movement distance of the support element 108 depends on the movement distance of the cam follower 107 in the cam groove 1062. The support element 108 becomes to be at a high location to be connected with the sample rack 5, and the light blocking plate 104 leaves the through slot of the optical coupler 102, such that the first rotary motor 111 stops rotating while the cam follower 107 stops moving in the cam groove 1062 (as shown in FIG. 10B). At this time, the second drive element 301 is started again to drive the first driving wheel 302 to rotate reversely (as shown in FIG. 11A). The first transmission belt 301 is driven by the first driven wheel 305 to move while driving the base 105 and the vertical movement member 1 mounted on the base 105 to move along the second guide rail 304 (the Y-axis direction) in a movement direction oriented toward the guide groove 308 and to finally arrive at the arrangement position of the guide groove 308 (as shown in FIG. 11B). At this time, the third drive element 402 is started to drive the second driving wheel 403 to rotate, and the second transmission belt 404 is driven by the second driven wheel 406 to move while driving the support base 307 and the sample rack moving mechanism mounted on the support base 307 to move along the third guide rail 405 (the X-axis direction), so as to convey the sample rack 5 to the testing position. After the testing is completed, the third drive element 402 is started reversely to drive the sample rack 5 holding the tested sample to move reversely along the original path, and to finally return to the temporary storing section 2. At this time, the sensor 410 may send a control signal such that the temporary storing section 2 moves along the transverse direction and the sample rack 5 in the next grid 21 is aligned with the guide groove 308 so as to begin the next cycle.

The present disclosure further provides a sample analyzing equipment including the aforementioned sample rack conveying device capable of conveying the sample tubes holding collected sample, testing and analyzing the samples within the sample tubes. The whole equipment has a simple and compact structure, and high transmission accuracy, thus effectively ensuring that samples are conveyed to the target position and reliably ensuring the pathological examination and analysis.

What is described by the aforementioned embodiments and accompanying drawings of the present disclosure is merely the preferable embodiments of the present disclosure, and is not intended to limit the present disclosure. Any amendments, equivalent substitutions, or improvements and so on within the spirit and principle of the present disclosure should be included within the protection scope of the present disclosure.

What is claimed is:

1. A sample rack moving mechanism for moving a sample rack capable of holding one or more sample containers, wherein the sample rack moving mechanism comprises:
   a first drive element;
   a cam that comprises a curved contour and is fixedly connected to the first drive element, wherein the cam is capable of being driven by the first drive element to rotate;
   a cam follower that cooperates with the cam and moves along the curved contour of the cam;
   a second drive element;
   a support element that is fixedly connected to the cam follower, wherein the support element is capable of being driven by the cam follower to move vertically, so that the support element is capable of being attached to or detached from the sample rack, wherein the support element is capable of being driven by the second drive element to move substantially horizontally, so that the sample rack can be moved horizontally together with the support element; and
   a guide groove for holding and guiding the sample rack, wherein a length direction of the guide groove is the same as the substantially horizontal moving direction of the support element, wherein the support element is capable of driving the sample rack to substantially horizontally move along the guide groove.

2. The sample rack moving mechanism according to claim 1, wherein the first drive element is a first rotary motor, the cam is a disk-shaped component and is eccentrically disposed on an output shaft of the first rotary motor, wherein the cam is driven to rotate by the first rotary motor; the cam comprises a cam groove, wherein the cam follower is inserted within the cam groove and is slidable within the cam groove.

3. The sample rack moving mechanism according to claim 2, wherein the cam comprises a kidney-shaped outer contour, and the cam groove is an arc-shaped groove penetrating through the disk-shaped component along an axial direction and is located adjacent to the kidney-shaped outer contour of the cam.

4. The sample rack moving mechanism according to claim 1, further comprising a support base for support the sample rack moving mechanism, wherein the second drive element is a second rotary motor fixed at one end of the support base and the support element is driven indirectly via a transmission by the second rotary motor;
   wherein the transmission mechanism comprises a first driving wheel disposed on an output shaft of the second rotary motor, and a first driven wheel fixed at an opposite end of the support base;
   wherein a transmission belt is connected between the first driving wheel and the first driven wheel, and is connected with the support element; and
   wherein a second guide rail is disposed in parallel with a transmission direction of the transmission belt, and a length direction of the second guide rail is substantially same as the horizontally moving direction of the support element, and the support element together with the cam and the cam follower are guided along the second guide rail, such that the sample rack attached to the support element is capable of being moved into or out of the guide groove.

5. The sample rack moving mechanism according to claim 1, wherein the support element is a fork-shaped element that is capable of substantially horizontally moving the sample rack; and the fork-shaped element comprises an opening, in which the sample rack is to be held.

6. The sample rack moving mechanism according to claim 5, wherein the fork-shaped element comprises two claws respectively provided at two sides of the opening, and the sample rack is to be held between the two claws in the opening.

7. The sample rack moving mechanism according to claim 1, wherein the first drive element is a first rotary motor that is fixed on a first mounting plate, a first guide rail is disposed on the first mounting plate, and the support element is guided along the first guide rail to move vertically so as to be attached to or detached from the sample rack.

8. The sample rack moving mechanism according to claim 7, wherein an optical coupler is disposed on the first mounting plate, and a light blocking plate capable of cooperating with the optical coupler is disposed on the support element, wherein the light blocking plate is used to trigger the optical coupler to control the first rotary motor to be turned on or off.

9. A sample rack conveying device, comprising:
a storing mechanism capable of being loaded with one or more sample racks, each sample rack is capable of being loaded with one or more containers;
a sample rack moving mechanism supported by a support base and configured to remove a sample rack on the storing mechanism from its holding position and/or return a sample rack to the storing mechanism, wherein the sample rack moving mechanism comprises:
a first drive element;
a cam that comprises a curved contour and is fixedly connected to the first drive element, wherein the cam is capable of being driven by the first drive element to rotate;
a cam follower that cooperates with the cam and moves along the curved contour of the cam;
a second drive element;
a support element that is fixedly connected to the cam follower, wherein the support element is capable of being driven by the cam follower to move vertically so that the support element is capable of being attached to or detached from the sample racks, wherein the support element is capable of being driven by the second drive element to move substantially horizontally, so that the sample rack can be moved horizontally together with the support element;
a guide groove for holding and guiding the sample rack, wherein a length direction of the guide groove is the same as the substantially horizontal moving direction of the support element, wherein the support element is capable of driving the sample rack to substantially horizontally move along the guide groove; and
a conveying member capable of conveying the support base for supporting the guide groove along a direction substantially perpendicular to the length direction of the guide groove.

10. The sample rack conveying device according to claim 9, wherein the conveying member comprises a third drive element and a third guide rail, and the support base for supporting the guide groove is driven by the third drive element to move along the third guide rail, so as to convey the sample rack held in the guide groove to or from a testing mechanism.

11. The sample rack conveying device according to claim 9, wherein the storing section comprises a through slot, the support element is capable of being inserted into the through slot, such that the support element is capable of being attached to a bottom of each sample rack via the through slot.

12. The sample rack conveying device according to claim 9, wherein the one or more sample racks are arranged in parallel along a direction substantially perpendicular to the length direction of the guide groove on the storing mechanism, a gear rack is disposed on one side of the storing mechanism along the direction substantially perpendicular to the length direction of the guide groove, wherein the gear rack are provided with one or more tooth slots, an amount of which equals to that of the sample racks arranged on the storing mechanism, and a sensor is disposed at one end of the gear rack and provides a sensing signal for controlling a movement of the guide groove.

13. The sample rack conveying device according to claim 9, wherein the first drive element is a first rotary motor, the cam is a disk-shaped component and is eccentrically disposed on an output shaft of the first rotary motor, wherein the cam is driven to rotate by the first rotary motor; the cam comprises a cam groove, wherein the cam follower is inserted within the cam groove and is slidable within the cam groove.

14. The sample rack conveying device according to claim 13, wherein the cam comprises a kidney-shaped outer contour, and the cam groove is an arc-shaped groove penetrating through the disk-shaped component along an axial direction and is located adjacent to the kidney-shaped outer contour of the cam.

15. The sample rack conveying device according to claim 9,
wherein the second drive element is a second rotary motor fixed at one end of a support base of the sample rack moving mechanism and the support element is driven indirectly via a transmission by the second rotary motor;
wherein the transmission mechanism comprises a first driving wheel disposed on an output shaft of the second rotary motor, and a first driven wheel fixed at an opposite end of the support base;
wherein a transmission belt is connected between the first driving wheel and the first driven wheel, and is connected with the support element; and
wherein a second guide rail is disposed in parallel with a transmission direction of the transmission belt, and a length direction of the second guide rail is substantially same as the horizontally moving direction of the support element, and the support element together with the cam and the cam follower are guided along the second guide rail, such that the sample rack attached to the support element is capable of being moved into or out of the guide groove.

16. The sample rack conveying device according to claim 9, wherein the support element is a fork-shaped element that is capable of substantially horizontally moving the sample rack; and the fork-shaped element comprises an opening, in which the sample rack is to be held.

17. The sample rack conveying device according to claim 16, wherein the fork-shaped element comprises two claws respectively provided at two sides of the opening, and the sample rack is to be held between the two claws in the opening.

18. The sample rack conveying device according to claim 9, wherein the first drive element is a first rotary motor that is fixed on a first mounting plate, a first guide rail is disposed on the first mounting plate, and the support element is guided along the first guide rail to move vertically so as to be attached to or detached from the sample rack.

19. The sample rack conveying device according to claim 18, wherein an optical coupler is disposed on the first mounting plate, and a light blocking plate capable of cooperating with the optical coupler is disposed on the support element, wherein the light blocking plate is used to trigger the optical coupler to control the first rotary motor to be turned on or off.

20. A sample analyzing equipment for conveying a sample rack capable of being loaded one or more sample containers holding a sample, testing and analyzing the sample, the equipment comprising:
   a testing mechanism for testing the sample; and
   a sample rack conveying device according to claim 9, wherein the sample rack conveying device is configured to convey the sample rack from the storing mechanism to the testing mechanism for testing and return the sample rack from the testing mechanism to the storing mechanism after testing.

\* \* \* \* \*